(12) United States Patent
Layman

(10) Patent No.: US 8,604,398 B1
(45) Date of Patent: Dec. 10, 2013

(54) MICROWAVE PURIFICATION PROCESS

(75) Inventor: Fredrick P. Layman, Carefree, AZ (US)

(73) Assignee: SDCmaterials, Inc., Tempe, AZ (US)

(*) Notice: Subject to any disclaimer, the term of this patent is extended or adjusted under 35 U.S.C. 154(b) by 455 days.

(21) Appl. No.: 12/943,909

(22) Filed: Nov. 10, 2010

Related U.S. Application Data

(62) Division of application No. 12/152,095, filed on May 9, 2008, now Pat. No. 7,905,942.

(60) Provisional application No. 60/928,946, filed on May 11, 2007.

(51) Int. Cl.
*H05B 6/64* (2006.01)
*C22B 9/14* (2006.01)

(52) U.S. Cl.
USPC .. 219/678; 219/121.41; 75/345; 118/723 ME

(58) Field of Classification Search
USPC ............... 219/678, 759, 688, 121.41; 75/345, 75/10.13, 585; 423/298, 186, 422, 651; 438/488, 57; 216/67; 118/723 AN, 118/723 E, 723 I, 723 ME, 715
See application file for complete search history.

(56) References Cited

U.S. PATENT DOCUMENTS

| | | | |
|---|---|---|---|
| 2,284,554 A | 5/1942 | Beyerstedt | |
| 2,419,042 A | 4/1947 | Todd | 202/205 |
| 2,519,531 A | 8/1950 | Worn | 230/95 |
| 2,562,753 A | 7/1951 | Trost | 241/39 |
| 2,689,780 A | 9/1954 | Rice | 23/106 |
| 3,001,402 A | 9/1961 | Koblin | 73/421.5 |
| 3,042,511 A | 7/1962 | Reding, Jr. | |
| 3,067,025 A | 12/1962 | Chisholm | 75/84.5 |
| 3,145,287 A | 8/1964 | Siebein et al. | |
| 3,178,121 A | 4/1965 | Wallace, Jr. | 241/5 |
| 3,179,782 A | 4/1965 | Matvay | |
| 3,313,908 A | 4/1967 | Unger et al. | |
| 3,401,465 A | 9/1968 | Larwill | 34/57 |

(Continued)

FOREIGN PATENT DOCUMENTS

| | | |
|---|---|---|
| EP | 1 619 168 A1 | 1/2006 |
| GB | 1 307 941 A | 2/1973 |

(Continued)

OTHER PUBLICATIONS

Derwent English Abstract for publication No. SU 193241 A, Application No. 1973SU1943286 filed on Jul. 2, 1973, published on Mar. 1, 1976, entitled "Catalyst for Ammonia Synthesis Contains Oxides of Aluminium, Potassium, Calcium, Iron and Nickel Oxide for Increased Activity," 3 pgs.

(Continued)

*Primary Examiner* — Quang Van

(74) *Attorney, Agent, or Firm* — Morrison & Foerster LLP

(57) ABSTRACT

A method of purifying a target powder having an oxygen content, the method comprising: flowing hydrogen gas through a microwave production chamber; applying microwaves to the hydrogen gas as the hydrogen gas flows through the microwave production chamber, thereby forming hydrogen radicals from the hydrogen gas; flowing the hydrogen radicals out of the microwave production chamber to the target powder disposed outside of the microwave production chamber; and applying the hydrogen radicals to the target powder, thereby removing a portion of the oxygen content from the powder. Preferably, the target powder is agitated as the hydrogen radicals are being applied.

7 Claims, 7 Drawing Sheets

(56) References Cited

U.S. PATENT DOCUMENTS

| | | | |
|---|---|---|---|
| 3,450,926 A | 6/1969 | Kiernan | |
| 3,457,788 A | 7/1969 | Miyajima | 73/422 |
| 3,537,513 A | 11/1970 | Austin | 165/70 |
| 3,552,653 A | 1/1971 | Inoue | |
| 3,617,358 A | 11/1971 | Dittrich | |
| 3,667,111 A | 6/1972 | Chartet | |
| 3,741,001 A | 6/1973 | Fletcher et al. | 73/28 |
| 3,752,172 A | 8/1973 | Cohen et al. | 137/12 |
| 3,761,360 A | 9/1973 | Auvil et al. | |
| 3,774,442 A | 11/1973 | Gustavsson | 73/28 |
| 3,830,756 A | 8/1974 | Sanchez et al. | |
| 3,871,448 A | 3/1975 | Vann et al. | |
| 3,892,882 A | 7/1975 | Guest et al. | 427/34 |
| 3,914,573 A | 10/1975 | Muehlberger | 219/76 |
| 3,959,094 A | 5/1976 | Steinberg | |
| 3,959,420 A | 5/1976 | Geddes et al. | 261/112 |
| 3,969,482 A | 7/1976 | Teller | |
| 4,008,620 A | 2/1977 | Narato et al. | 73/421.5 A |
| 4,018,388 A | 4/1977 | Andrews | 241/39 |
| 4,021,021 A | 5/1977 | Hall et al. | |
| 4,139,497 A | 2/1979 | Castor et al. | 252/470 |
| 4,157,316 A | 6/1979 | Thompson et al. | |
| 4,171,288 A | 10/1979 | Keith et al. | 252/462 |
| 4,174,298 A | 11/1979 | Antos | |
| 4,227,928 A | 10/1980 | Wang | |
| 4,248,387 A | 2/1981 | Andrews | 241/5 |
| 4,253,917 A | 3/1981 | Wang | |
| 4,284,609 A | 8/1981 | deVries | 423/242 |
| 4,344,779 A | 8/1982 | Isserlis | |
| 4,369,167 A | 1/1983 | Weir | |
| 4,388,274 A | 6/1983 | Rourke et al. | 422/177 |
| 4,419,331 A | 12/1983 | Montalvo | |
| 4,431,750 A | 2/1984 | McGinnis et al. | |
| 4,436,075 A | 3/1984 | Campbell et al. | 123/557 |
| 4,440,733 A | 4/1984 | Lawson et al. | |
| 4,458,138 A | 7/1984 | Adrian et al. | |
| 4,459,327 A | 7/1984 | Wang | |
| 4,505,945 A | 3/1985 | Dubust et al. | |
| 4,513,149 A | 4/1985 | Gray et al. | 564/449 |
| RE32,244 E | 9/1986 | Andersen | |
| 4,609,441 A | 9/1986 | Frese, Jr. et al. | |
| 4,723,589 A | 2/1988 | Iyer et al. | |
| 4,731,517 A | 3/1988 | Cheney | |
| 4,764,283 A | 8/1988 | Ashbrook et al. | 210/695 |
| 4,765,805 A | 8/1988 | Wahl et al. | |
| 4,824,624 A | 4/1989 | Palicka et al. | 264/67 |
| 4,855,505 A | 8/1989 | Koll | 564/398 |
| 4,866,240 A | 9/1989 | Webber | 219/121.47 |
| 4,885,038 A | 12/1989 | Anderson et al. | |
| 4,921,586 A | 5/1990 | Molter | |
| 4,983,555 A | 1/1991 | Roy et al. | 501/120 |
| 4,987,033 A | 1/1991 | Abkowitz et al. | 428/469 |
| 5,015,863 A | 5/1991 | Takeshima et al. | |
| 5,041,713 A | 8/1991 | Weidman | 219/121.51 |
| 5,043,548 A | 8/1991 | Whitney et al. | 219/121.84 |
| 5,070,064 A | 12/1991 | Hsu et al. | |
| 5,073,193 A | 12/1991 | Chaklader et al. | 75/346 |
| 5,133,190 A | 7/1992 | Abdelmalek | |
| 5,151,296 A * | 9/1992 | Tokunaga | 438/488 |
| 5,157,007 A | 10/1992 | Domesle et al. | |
| 5,230,844 A | 7/1993 | Macaire et al. | |
| 5,233,153 A | 8/1993 | Coats | |
| 5,269,848 A * | 12/1993 | Nakagawa | 118/723 ME |
| 5,338,716 A | 8/1994 | Triplett et al. | |
| 5,369,241 A | 11/1994 | Taylor et al. | 219/121.47 |
| 5,371,049 A | 12/1994 | Moffett et al. | 501/89 |
| 5,372,629 A | 12/1994 | Anderson et al. | 75/332 |
| 5,392,797 A | 2/1995 | Welch | 134/108 |
| 5,439,865 A | 8/1995 | Abe et al. | 502/333 |
| 5,442,153 A | 8/1995 | Marantz et al. | 219/121.47 |
| 5,460,701 A | 10/1995 | Parker et al. | |
| 5,464,458 A | 11/1995 | Yamamoto | |
| 5,485,941 A | 1/1996 | Guyomard et al. | 222/1 |
| 5,534,149 A | 7/1996 | Birkenbeil et al. | 210/636 |
| 5,553,507 A | 9/1996 | Basch et al. | 73/863.01 |
| 5,562,966 A | 10/1996 | Clarke et al. | |
| 5,582,807 A | 12/1996 | Liao et al. | |
| 5,611,896 A | 3/1997 | Swanepoel et al. | 204/169 |
| 5,630,322 A | 5/1997 | Heilmann et al. | 62/95 |
| 5,652,304 A | 7/1997 | Mizrahi | |
| 5,714,644 A | 2/1998 | Irgang et al. | |
| 5,723,187 A | 3/1998 | Popoola et al. | |
| 5,726,414 A | 3/1998 | Kitahashi et al. | |
| 5,749,938 A | 5/1998 | Coombs | 75/332 |
| 5,776,359 A | 7/1998 | Schultz et al. | 252/62.51 |
| 5,788,738 A | 8/1998 | Pirzada et al. | 75/331 |
| 5,811,187 A | 9/1998 | Anderson et al. | 428/403 |
| 5,837,959 A | 11/1998 | Muehlberger et al. | 219/121.47 |
| 5,851,507 A | 12/1998 | Pirzada et al. | 423/659 |
| 5,853,815 A | 12/1998 | Muehlberger | 427/446 |
| 5,858,470 A | 1/1999 | Bernecki et al. | |
| 5,905,000 A | 5/1999 | Yadav et al. | 429/33 |
| 5,928,806 A | 7/1999 | Olah et al. | |
| 5,935,293 A | 8/1999 | Detering et al. | 75/10.29 |
| 5,973,289 A | 10/1999 | Read et al. | |
| 5,989,648 A | 11/1999 | Phillips | 427/456 |
| 5,993,967 A | 11/1999 | Brotzman, Jr. et al. | 428/407 |
| 5,993,988 A | 11/1999 | Ohara et al. | 429/40 |
| 6,004,620 A | 12/1999 | Camm | |
| 6,012,647 A | 1/2000 | Ruta et al. | 239/132.1 |
| 6,033,781 A | 3/2000 | Brotzman, Jr. et al. | 428/405 |
| 6,045,765 A | 4/2000 | Nakatsuji et al. | |
| 6,059,853 A | 5/2000 | Coombs | 75/332 |
| 6,084,197 A | 7/2000 | Fusaro, Jr. | |
| 6,093,306 A | 7/2000 | Hanrahan et al. | |
| 6,102,106 A | 8/2000 | Manning et al. | 165/76 |
| 6,117,376 A | 9/2000 | Merkel | |
| 6,213,049 B1 | 4/2001 | Yang | 118/723 |
| 6,214,195 B1 | 4/2001 | Yadav et al. | 205/334 |
| 6,228,904 B1 | 5/2001 | Yadav et al. | 523/210 |
| 6,254,940 B1 | 7/2001 | Pratsinis et al. | 427/562 |
| 6,261,484 B1 | 7/2001 | Phillips et al. | 264/5 |
| 6,267,864 B1 | 7/2001 | Yadav et al. | 205/341 |
| 6,322,756 B1 | 11/2001 | Arno et al. | |
| 6,342,465 B1 | 1/2002 | Klein et al. | |
| 6,344,271 B1 | 2/2002 | Yadav et al. | 428/402 |
| 6,379,419 B1 | 4/2002 | Celik et al. | 75/346 |
| 6,387,560 B1 | 5/2002 | Yadav et al. | 429/45 |
| 6,395,214 B1 | 5/2002 | Kear et al. | 264/434 |
| 6,398,843 B1 | 6/2002 | Tarrant | 75/249 |
| 6,409,851 B1 | 6/2002 | Sethuram et al. | 148/565 |
| 6,413,781 B1 | 7/2002 | Geis et al. | 436/178 |
| 6,416,818 B1 | 7/2002 | Aikens et al. | 427/383.1 |
| RE37,853 E | 9/2002 | Detering et al. | 75/10.19 |
| 6,444,009 B1 | 9/2002 | Liu et al. | 75/332 |
| 6,475,951 B1 | 11/2002 | Domesle et al. | |
| 6,506,995 B1 | 1/2003 | Fusaro, Jr. et al. | |
| 6,517,800 B1 | 2/2003 | Cheng et al. | 423/447.1 |
| 6,524,662 B2 | 2/2003 | Jang et al. | 427/535 |
| 6,531,704 B2 | 3/2003 | Yadav et al. | 250/493.1 |
| 6,548,445 B1 | 4/2003 | Buysch et al. | |
| 6,554,609 B2 | 4/2003 | Yadav et al. | 432/9 |
| 6,562,304 B1 | 5/2003 | Mizrahi | |
| 6,562,495 B2 | 5/2003 | Yadav et al. | 429/12 |
| 6,569,397 B1 | 5/2003 | Yadav et al. | 423/345 |
| 6,569,518 B2 | 5/2003 | Yadav et al. | 428/323 |
| 6,572,672 B2 | 6/2003 | Yadav et al. | 75/343 |
| 6,579,446 B1 | 6/2003 | Teran et al. | |
| 6,596,187 B2 | 7/2003 | Coll et al. | 216/56 |
| 6,603,038 B1 | 8/2003 | Hagemeyer et al. | 560/241.1 |
| 6,607,821 B2 | 8/2003 | Yadav et al. | 428/323 |
| 6,610,355 B2 | 8/2003 | Yadav et al. | 427/115 |
| 6,623,559 B2 | 9/2003 | Huang | 117/87 |
| 6,635,357 B2 | 10/2003 | Moxson et al. | 428/548 |
| 6,641,775 B2 | 11/2003 | Vigliotti et al. | 264/618 |
| 6,652,822 B2 | 11/2003 | Phillips et al. | 423/290 |
| 6,652,967 B2 | 11/2003 | Yadav et al. | 428/403 |
| 6,669,823 B1 | 12/2003 | Sarkas et al. | 204/164 |
| 6,682,002 B2 | 1/2004 | Kyotani | 239/318 |
| 6,689,192 B1 | 2/2004 | Phillips et al. | 75/342 |
| 6,699,398 B1 | 3/2004 | Kim | 216/55 |
| 6,706,097 B2 | 3/2004 | Zornes | 96/153 |
| 6,706,660 B2 | 3/2004 | Park | |
| 6,710,207 B2 | 3/2004 | Bogan, Jr. et al. | |

(56) References Cited

U.S. PATENT DOCUMENTS

| | | | |
|---|---|---|---|
| 6,713,176 B2 | 3/2004 | Yadav et al. | 428/402 |
| 6,716,525 B1 | 4/2004 | Yadav et al. | 428/402 |
| 6,744,006 B2 | 6/2004 | Johnson et al. | |
| 6,746,791 B2 | 6/2004 | Yadav et al. | 429/30 |
| 6,772,584 B2 | 8/2004 | Chun et al. | 60/275 |
| 6,786,950 B2 | 9/2004 | Yadav et al. | 75/346 |
| 6,813,931 B2 | 11/2004 | Yadav et al. | 73/31.05 |
| 6,817,388 B2 | 11/2004 | Tsangaris et al. | 141/82 |
| 6,832,735 B2 | 12/2004 | Yadav et al. | 241/16 |
| 6,838,072 B1 | 1/2005 | Kong et al. | 423/594.2 |
| 6,841,509 B1 | 1/2005 | Hwang et al. | |
| 6,855,410 B2 | 2/2005 | Buckley | |
| 6,855,426 B2 | 2/2005 | Yadav | 428/403 |
| 6,855,749 B1 | 2/2005 | Yadav et al. | 523/105 |
| 6,886,545 B1 | 5/2005 | Holm | 123/568.21 |
| 6,896,958 B1 | 5/2005 | Cayton et al. | 428/323 |
| 6,902,699 B2 | 6/2005 | Fritzemeier et al. | 419/38 |
| 6,916,872 B2 | 7/2005 | Yadav et al. | 524/430 |
| 6,919,065 B2 | 7/2005 | Zhou et al. | |
| 6,919,527 B2 | 7/2005 | Boulos et al. | 219/121.52 |
| 6,933,331 B2 | 8/2005 | Yadav et al. | 523/210 |
| 6,972,115 B1 | 12/2005 | Ballard | |
| 6,986,877 B2 | 1/2006 | Takikawa et al. | 423/447.3 |
| 6,994,837 B2 | 2/2006 | Boulos et al. | 423/613 |
| 7,007,872 B2 | 3/2006 | Yadav et al. | 241/1 |
| 7,022,305 B2 | 4/2006 | Drumm et al. | |
| 7,052,777 B2 | 5/2006 | Brotzman, Jr. et al. | 428/570 |
| 7,073,559 B2 | 7/2006 | O'Larey et al. | 164/76.1 |
| 7,081,267 B2 | 7/2006 | Yadav | 427/115 |
| 7,101,819 B2 | 9/2006 | Rosenflanz et al. | 501/10 |
| 7,147,544 B2 | 12/2006 | Rosenflanz | 451/28 |
| 7,147,894 B2 | 12/2006 | Zhou et al. | 427/256 |
| 7,166,198 B2 | 1/2007 | Van Der Walt et al. | 204/165 |
| 7,166,663 B2 | 1/2007 | Cayton et al. | 524/430 |
| 7,172,649 B2 | 2/2007 | Conrad et al. | 106/35 |
| 7,172,790 B2 | 2/2007 | Koulik et al. | |
| 7,178,747 B2 | 2/2007 | Yadav et al. | 241/23 |
| 7,208,126 B2 | 4/2007 | Musick et al. | 423/69 |
| 7,211,236 B2 | 5/2007 | Stark et al. | 423/592.1 |
| 7,217,407 B2 | 5/2007 | Zhang | 423/610 |
| 7,220,398 B2 | 5/2007 | Sutorik et al. | 423/593.1 |
| 7,255,498 B2 | 8/2007 | Bush et al. | |
| 7,265,076 B2 | 9/2007 | Taguchi et al. | |
| 7,307,195 B2 | 12/2007 | Polverejan et al. | 585/443 |
| 7,323,655 B2 | 1/2008 | Kim | 219/121.43 |
| 7,384,447 B2 | 6/2008 | Kodas et al. | 75/332 |
| 7,402,899 B1 | 7/2008 | Whiting et al. | |
| 7,417,008 B2 | 8/2008 | Richards et al. | |
| 7,494,527 B2 | 2/2009 | Jurewicz et al. | 75/346 |
| 7,517,826 B2 | 4/2009 | Fujdala et al. | |
| 7,534,738 B2 | 5/2009 | Fujdala et al. | |
| 7,541,012 B2 | 6/2009 | Yeung et al. | |
| 7,541,310 B2 | 6/2009 | Espinoza et al. | |
| 7,557,324 B2 | 7/2009 | Nylen et al. | |
| 7,572,315 B2 | 8/2009 | Boulos et al. | 75/336 |
| 7,611,686 B2 | 11/2009 | Alekseeva et al. | 423/276 |
| 7,615,097 B2 | 11/2009 | McKechnie et al. | 75/346 |
| 7,618,919 B2 | 11/2009 | Shimazu et al. | |
| 7,622,693 B2 | 11/2009 | Foret | 219/121.43 |
| 7,632,775 B2 | 12/2009 | Zhou et al. | |
| 7,674,744 B2 | 3/2010 | Shiratori et al. | |
| 7,678,419 B2 | 3/2010 | Kevwitch et al. | |
| 7,709,411 B2 | 5/2010 | Zhou et al. | |
| 7,709,414 B2 | 5/2010 | Fujdala et al. | |
| 7,745,367 B2 | 6/2010 | Fujdala et al. | |
| 7,750,265 B2 | 7/2010 | Belashchenko et al. | |
| 7,803,210 B2 | 9/2010 | Sekine et al. | 75/334 |
| 7,851,405 B2 | 12/2010 | Wakamatsu et al. | |
| 7,874,239 B2 | 1/2011 | Howland | |
| 7,897,127 B2 | 3/2011 | Layman et al. | |
| 7,902,104 B2 | 3/2011 | Kalck | |
| 7,905,942 B1 | 3/2011 | Layman | |
| 7,935,655 B2 | 5/2011 | Tolmachev | |
| 8,051,724 B1 | 11/2011 | Layman et al. | |
| 8,076,258 B1 | 12/2011 | Biberger | |
| 8,080,494 B2 | 12/2011 | Yasuda et al. | |
| 8,089,495 B2 | 1/2012 | Keller | |
| 8,142,619 B2 | 3/2012 | Layman et al. | |
| 8,168,561 B2 | 5/2012 | Virkar | |
| 8,173,572 B2 | 5/2012 | Feaviour | |
| 8,258,070 B2 | 9/2012 | Fujdala et al. | |
| 8,278,240 B2 | 10/2012 | Tange et al. | |
| 8,294,060 B2 | 10/2012 | Mohanty et al. | |
| 8,309,489 B2 | 11/2012 | Cuenya et al. | |
| 8,349,761 B2 | 1/2013 | Xia et al. | |
| 2001/0004009 A1 | 6/2001 | MacKelvie | |
| 2001/0042802 A1 | 11/2001 | Youds | 241/5 |
| 2002/0018815 A1 | 2/2002 | Sievers et al. | 424/489 |
| 2002/0068026 A1 | 6/2002 | Murrell et al. | 422/211 |
| 2002/0079620 A1 | 6/2002 | DuBuis et al. | 264/328.14 |
| 2002/0100751 A1 | 8/2002 | Carr | |
| 2002/0102674 A1 | 8/2002 | Anderson | 435/174 |
| 2002/0131914 A1 | 9/2002 | Sung | |
| 2002/0143417 A1 | 10/2002 | Ito et al. | |
| 2002/0182735 A1 | 12/2002 | Kibby et al. | |
| 2002/0183191 A1 | 12/2002 | Faber et al. | |
| 2002/0192129 A1 | 12/2002 | Shamouilian et al. | |
| 2003/0036786 A1 | 2/2003 | Duren et al. | 607/96 |
| 2003/0042232 A1 | 3/2003 | Shimazu | 219/121.47 |
| 2003/0047617 A1 | 3/2003 | Shanmugham et al. | |
| 2003/0066800 A1 | 4/2003 | Saim et al. | 264/5 |
| 2003/0108459 A1 | 6/2003 | Wu et al. | 422/186.04 |
| 2003/0110931 A1 | 6/2003 | Aghajanian et al. | |
| 2003/0139288 A1 | 7/2003 | Cai et al. | |
| 2003/0143153 A1 | 7/2003 | Boulos et al. | |
| 2003/0172772 A1 | 9/2003 | Sethuram et al. | 501/87 |
| 2003/0223546 A1 | 12/2003 | McGregor et al. | 378/143 |
| 2004/0009118 A1 | 1/2004 | Phillips et al. | 423/592.1 |
| 2004/0023302 A1 | 2/2004 | Archibald et al. | 435/7.1 |
| 2004/0023453 A1 | 2/2004 | Xu et al. | 257/369 |
| 2004/0077494 A1 | 4/2004 | LaBarge et al. | 502/303 |
| 2004/0103751 A1 | 6/2004 | Joseph et al. | 75/10.19 |
| 2004/0109523 A1 | 6/2004 | Singh et al. | |
| 2004/0119064 A1 | 6/2004 | Narayan et al. | |
| 2004/0127586 A1 | 7/2004 | Jin et al. | |
| 2004/0167009 A1 | 8/2004 | Kuntz et al. | 501/95.2 |
| 2004/0176246 A1 | 9/2004 | Shirk et al. | 502/439 |
| 2004/0208805 A1 | 10/2004 | Fincke et al. | |
| 2004/0213998 A1 | 10/2004 | Hearley et al. | 428/402 |
| 2004/0238345 A1 | 12/2004 | Koulik et al. | |
| 2004/0251017 A1 | 12/2004 | Pillion et al. | 165/289 |
| 2004/0251241 A1 | 12/2004 | Blutke et al. | |
| 2005/0000321 A1 | 1/2005 | O'Larey et al. | 75/952 |
| 2005/0000950 A1 | 1/2005 | Schroder et al. | 219/121.59 |
| 2005/0066805 A1 | 3/2005 | Park et al. | |
| 2005/0070431 A1 | 3/2005 | Alvin et al. | |
| 2005/0077034 A1 | 4/2005 | King | 165/163 |
| 2005/0097988 A1 | 5/2005 | Kodas et al. | 75/332 |
| 2005/0106865 A1 | 5/2005 | Chung et al. | |
| 2005/0163673 A1 | 7/2005 | Johnson et al. | |
| 2005/0199739 A1 | 9/2005 | Kuroda et al. | 239/13 |
| 2005/0220695 A1 | 10/2005 | Abatzoglou et al. | 423/445 |
| 2005/0227864 A1 | 10/2005 | Sutorik et al. | |
| 2005/0233380 A1 | 10/2005 | Pesiri et al. | 435/7.1 |
| 2005/0240069 A1 | 10/2005 | Polverejan et al. | 585/444 |
| 2005/0258766 A1 | 11/2005 | Kim | 315/111.21 |
| 2005/0275143 A1 | 12/2005 | Toth | |
| 2006/0051505 A1 | 3/2006 | Kortshagen et al. | 427/212 |
| 2006/0068989 A1 | 3/2006 | Ninomiya et al. | 502/339 |
| 2006/0094595 A1 | 5/2006 | Labarge | |
| 2006/0096393 A1 | 5/2006 | Pesiri | 73/863.21 |
| 2006/0105910 A1 | 5/2006 | Zhou et al. | 502/338 |
| 2006/0108332 A1 | 5/2006 | Belashchenko | 219/121.47 |
| 2006/0153728 A1 | 7/2006 | Schoenung et al. | 419/32 |
| 2006/0153765 A1 | 7/2006 | Pham-Huu et al. | 423/345 |
| 2006/0159596 A1 | 7/2006 | De La Veaux et al. | 422/151 |
| 2006/0166809 A1 | 7/2006 | Malek et al. | |
| 2006/0222780 A1 | 10/2006 | Gurevich et al. | |
| 2006/0231525 A1 | 10/2006 | Asakawa et al. | 216/56 |
| 2007/0048206 A1 | 3/2007 | Hung et al. | 423/335 |
| 2007/0049484 A1 | 3/2007 | Kear et al. | |
| 2007/0063364 A1 | 3/2007 | Hsiao et al. | 264/5 |
| 2007/0084308 A1 | 4/2007 | Nakamura et al. | 75/346 |
| 2007/0084834 A1 | 4/2007 | Hanus et al. | 219/121.5 |

(56) References Cited

U.S. PATENT DOCUMENTS

| | | | |
|---|---|---|---|
| 2007/0087934 A1 | 4/2007 | Martens et al. | 502/214 |
| 2007/0163385 A1 | 7/2007 | Takahashi et al. | |
| 2007/0173403 A1 | 7/2007 | Koike et al. | 502/300 |
| 2007/0178673 A1 | 8/2007 | Gole et al. | |
| 2007/0221404 A1 | 9/2007 | Das et al. | |
| 2007/0253874 A1 | 11/2007 | Foret | 422/186.07 |
| 2007/0292321 A1 | 12/2007 | Plischke et al. | 422/198 |
| 2008/0006954 A1 | 1/2008 | Yubuta et al. | |
| 2008/0031806 A1 | 2/2008 | Gavenonis et al. | |
| 2008/0038578 A1 | 2/2008 | Li | |
| 2008/0047261 A1 | 2/2008 | Han et al. | |
| 2008/0057212 A1 | 3/2008 | Dorier et al. | |
| 2008/0064769 A1 | 3/2008 | Sato et al. | |
| 2008/0105083 A1 | 5/2008 | Nakamura et al. | 75/255 |
| 2008/0116178 A1 | 5/2008 | Weidman | 219/121.47 |
| 2008/0125308 A1 | 5/2008 | Fujdala et al. | |
| 2008/0125313 A1 | 5/2008 | Fujdala et al. | |
| 2008/0138651 A1 | 6/2008 | Doi et al. | |
| 2008/0175936 A1 | 7/2008 | Tokita et al. | |
| 2008/0187714 A1 | 8/2008 | Wakamatsu et al. | |
| 2008/0206562 A1 | 8/2008 | Stucky et al. | |
| 2008/0207858 A1 | 8/2008 | Kowaleski et al. | |
| 2008/0248704 A1 | 10/2008 | Mathis et al. | |
| 2008/0274344 A1 | 11/2008 | Vieth et al. | |
| 2008/0277092 A1 | 11/2008 | Layman et al. | |
| 2008/0277264 A1 | 11/2008 | Biberger et al. | |
| 2008/0277266 A1 | 11/2008 | Layman | |
| 2008/0277267 A1 | 11/2008 | Biberger et al. | 204/157.15 |
| 2008/0277268 A1 | 11/2008 | Layman | |
| 2008/0277269 A1 | 11/2008 | Layman et al. | |
| 2008/0277270 A1 | 11/2008 | Biberger et al. | |
| 2008/0277271 A1 | 11/2008 | Layman | |
| 2008/0280049 A1 | 11/2008 | Kevwitch et al. | |
| 2008/0280751 A1 | 11/2008 | Harutyunyan et al. | |
| 2008/0280756 A1 | 11/2008 | Biberger | |
| 2008/0283498 A1* | 11/2008 | Yamazaki | 216/67 |
| 2009/0010801 A1 | 1/2009 | Murphy et al. | |
| 2009/0054230 A1 | 2/2009 | Veeraraghavan et al. | |
| 2009/0088585 A1 | 4/2009 | Schammel et al. | |
| 2009/0092887 A1 | 4/2009 | McGrath et al. | |
| 2009/0114568 A1 | 5/2009 | Trevino et al. | |
| 2009/0162991 A1 | 6/2009 | Beneyton et al. | |
| 2009/0168506 A1 | 7/2009 | Han et al. | |
| 2009/0170242 A1 | 7/2009 | Lin et al. | |
| 2009/0181474 A1 | 7/2009 | Nagai | |
| 2009/0200180 A1 | 8/2009 | Capote et al. | |
| 2009/0223410 A1 | 9/2009 | Jun et al. | |
| 2009/0253037 A1 | 10/2009 | Park et al. | |
| 2009/0274903 A1 | 11/2009 | Addiego | |
| 2009/0286899 A1 | 11/2009 | Hofmann et al. | |
| 2010/0089002 A1 | 4/2010 | Merkel | |
| 2010/0275781 A1 | 11/2010 | Tsangaris | |
| 2011/0006463 A1 | 1/2011 | Layman | |
| 2011/0052467 A1 | 3/2011 | Chase et al. | |
| 2011/0143041 A1 | 6/2011 | Layman et al. | |
| 2011/0143915 A1 | 6/2011 | Yin et al. | |
| 2011/0143916 A1 | 6/2011 | Leamon | |
| 2011/0143926 A1 | 6/2011 | Leamon | |
| 2011/0143930 A1 | 6/2011 | Yin et al. | |
| 2011/0143933 A1 | 6/2011 | Yin et al. | |
| 2011/0144382 A1 | 6/2011 | Yin et al. | |
| 2011/0152550 A1 | 6/2011 | Grey et al. | |
| 2011/0158871 A1 | 6/2011 | Arnold et al. | |
| 2011/0174604 A1 | 7/2011 | Duesel et al. | |
| 2011/0245073 A1 | 10/2011 | Oljaca et al. | |
| 2011/0247336 A9 | 10/2011 | Farsad et al. | |
| 2012/0045373 A1 | 2/2012 | Biberger | |
| 2012/0097033 A1 | 4/2012 | Arnold et al. | |
| 2012/0122660 A1 | 5/2012 | Andersen et al. | |
| 2012/0171098 A1 | 7/2012 | Hung et al. | |
| 2012/0308467 A1 | 12/2012 | Carpenter et al. | |

FOREIGN PATENT DOCUMENTS

| | | |
|---|---|---|
| JP | 56-146804 | 11/1981 |
| JP | 61-086815 A | 5/1986 |
| JP | 63-214342 A | 9/1988 |
| JP | 1-164795 A | 6/1989 |
| JP | 05-228361 A | 9/1993 |
| JP | 05-324094 A | 12/1993 |
| JP | 6-93309 A | 4/1994 |
| JP | 6-135797 A | 5/1994 |
| JP | 6-65772 U | 9/1994 |
| JP | 6-272012 A | 9/1994 |
| JP | 7031873 A | 2/1995 |
| JP | 7-256116 A | 10/1995 |
| JP | 11-502760 A | 3/1999 |
| JP | 2000-220978 A | 8/2000 |
| JP | 2002-336688 A | 11/2002 |
| JP | 2004-233007 A | 8/2004 |
| JP | 2004-249206 A | 9/2004 |
| JP | 2004-290730 A | 10/2004 |
| JP | 2005-503250 A | 2/2005 |
| JP | 2005-122621 A | 5/2005 |
| JP | 2005-218937 A | 8/2005 |
| JP | 2005-342615 A | 12/2005 |
| JP | 2006-001779 A | 1/2006 |
| JP | 2006-508885 A | 3/2006 |
| JP | 2006-247446 A | 9/2006 |
| JP | 2006-260385 A | 9/2006 |
| JP | 2007-46162 A | 2/2007 |
| JP | 2007-203129 A | 8/2007 |
| SU | 493241 | 3/1976 |
| TW | 201023207 A | 6/2010 |
| WO | WO-96/28577 A1 | 9/1996 |
| WO | WO 02/092503 A1 | 11/2002 |
| WO | WO 2004/052778 A2 | 6/2004 |
| WO | WO-2005/063390 A1 | 7/2005 |
| WO | WO 2006/079213 A1 | 8/2006 |
| WO | WO-2008/130451 A2 | 10/2008 |
| WO | WO-2008/130451 A3 | 10/2008 |
| WO | WO-2011/081833 A1 | 7/2011 |

OTHER PUBLICATIONS

A. Gutsch et al., "Gas-Phase Production of Nanoparticles", Kona No. 20, 2002, pp. 24-37.

Dr. Heike Mühlenweg et al., "Gas-Phase Reactions—Open Up New Roads to Nanoproducts", Degussa ScienceNewsletter No. 08, 2004, pp. 12-16.

Coating Generation: Vaporization of Particles in Plasma Spraying and Splat Formation, M. Vardelle, A. Vardelle, K-I li, P. Fauchais, Universite de Limoges, 123 Avenue A. Thomas 87000, Limoges,F. , Pure & Chem, vol. 68, No. 5, pp. 1093-1099, 1996.

H. Konrad et al., "Nanostructured Cu-Bi Alloys Prepared by Co-Evaporation in a Continuous Gas Flow," NanoStructured Materials, vol. 7, No. 6, 1996, pp. 605-610.

Kenvin et al. "Supported Catalysts Prepared from Mononuclear Copper Complexes: Catalytic Properties", Journal of Catalysis, pp. 81-91, (1992).

J. Heberlein, "New Approaches in Thermal Plasma Technology", Pure Appl. Chem., vol. 74, No. 3, 2002, pp. 327-335.

M. Vardelle et al., "Experimental Investigation of Powder Vaporization in Thermal Plasma Jets," Plasma Chemistry and Plasma Processing, vol. 11, No. 2, Jun. 1991, pp. 185-201.

National Aeronautics and Space Administration, "Enthalpy", http://www.grc.nasa.gov/WWW/K-12/airplane/enthalpy.html, Nov. 23, 2009, 1 page.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

T. Yoshida, "The Future of Thermal Plasma Processing for Coating", Pure & Appl. Chem., vol. 66, No. 6, 1994 pp. 1223-1230.

(56) References Cited

OTHER PUBLICATIONS

Han et al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670&DOC=FILE.PDF., 6 pages.
Nagai, Yasutaka, et al. "Sintering Inhibition Mechanism of Platinum Supported on Ceria-based Oxide and Pt-oxide-support Interaction,"Journal of Catalysis 242 (2006), pp. 103-109, Jul. 3, 2006, Elsevier.
McGuthry Banks, Tima Michele, U.S. Patent and Trademark Office, Notice of Allowance mailed Nov. 24, 2010, for U.S. Appl. No. 12/152,095, 8 pgs.
Bateman, J. E. et al. (Dec. 17, 1998). "Alkylation of Porous Silicon by Direct Reaction with Alkenes and Alkynes," Angew. Chem Int. Ed. 37(19):2683-2685.
Carrot, G. et al. (Sep. 17, 2002). "Surface-Initiated Ring-Opening Polymerization: A Versatile Method for Nanoparticle Ordering," Macromolecules 35(22):8400-8404.
Chen, H.-S. et al. (Jul. 3, 2001). "On the Photoluminescence of Si Nanoparticles," Mater. Phys. Mech. 4:62-66.
Faber, K. T. et al. (Sep. 1988). "Toughening by Stress-Induced Microcracking in Two-Phase Ceramics," Communications of the American Ceramic Society 71(9): C-399-C401.
Fojtik, A. et al. (Apr. 29, 1994). "Luminescent Colloidal Silicon Particles,"Chemical Physics Letters 221:363-367.
Fojtik, A. (Jan. 13, 2006). "Surface Chemistry of Luminescent Colloidal Silicon Nanoparticles," J. Phys. Chem. B. 110(5):1994-1998.
Hua, F. et al. (Mar. 2006). "Organically Capped Silicon Nanoparticles With Blue Photoluminescence Prepared by Hydrosilylation Followed by Oxidation," Langmuir 22(9):4363-4370.
Ji, Y. et al. (Nov. 2002) "Processing and Mechanical Properties of Al2O3-5 vol.% Cr Nanocomposites," Journal of the European Ceramic Society 22(12):1927-1936.
Jouet, R. J. et al. (Jan. 25, 2005). "Surface Passivation of Bare Aluminum Nanoparticles Using Perfluoroalkyl Carboxylic Acids," Chem. Mater.17(11):2987-2996.
Kim, N. Y. et al. (Mar. 5, 1997). "Thermal Derivatization of Porous Silicon with Alcohols," J. Am. Chem. Soc. 119(9):2297-2298.
Kwon, Y.-S. et al. (Apr. 30, 2003). "Passivation Process for Superfine Aluminum Powders Obtained by Electrical Explosion of Wires," Applied Surface Science 211:57-67.
Langner, A. et al. (Aug. 25, 2005). "Controlled Silicon Surface Functionalization by Alkene Hydrosilylation," J. Am. Chem. Soc. 127(37):12798-12799.
Li, D. et al. (Apr. 9, 2005). "Environmentally Responsive "Hairy" Nanoparticles: Mixed Homopolymer Brushes on Silica Nanoparticles Synthesized by Living Radical Polymerization Techniques," J. Am. Chem. Soc. 127(7):6248-6256.
Li, X. et al. (May 25, 2004). "Surface Functionalization of Silicon Nanoparticles Produced by Laser-Driven Pyrolysis of Silane Followed by HF-HNO3 Etching," Langmuir 20(11):4720-4727.
Liao, Y.-C. et al. (Jun. 27, 2006). "Self-Assembly of Organic Monolayers on Aerosolized Silicon Nanoparticles," J.Am. Chem. Soc. 128(28):9061-9065.
Liu, S.-M. et al. (Jan. 13, 2006). "Enhanced Photoluminescence from Si Nano-Organosols by Functionalization With Alkenes and Their Size Evolution," Chem. Mater. 18(3):637-642.
Neiner, D. (Aug. 5, 2006). "Low-Temperature Solution Route to Macroscopic Amounts of Hydrogen Terminated Silicon Nanoparticles," J. Am. Chem. Soc. 128:11016-11017.
Netzer, L. et al. (1983). "A New Approach to Construction of Artificial Monolayer Assemblies," J. Am. Chem. Soc. 105(3):674-676.
"Platinum Group Metals: Annual Review 1996" (Oct. 1997). Engineering and Mining Journal, p. 63.
Rahaman, R. A. et al. (1995). "Synthesis of Powders," in Ceramic Processing and Sintering. Marcel Decker, Inc., New York, pp. 71-77.
Sailor, M. J. (1997). "Surface Chemistry of Luminescent Silicon Nanocrystallites," Adv. Mater. 9(10):783-793.
Stiles, A. B. (Jan. 1, 1987). "Manufacture of Carbon-Supported Metal Catalysts," in Catalyst Supports and Supported Catalysts, Butterworth Publishers, MA, pp. 125-132.
Subramanian, S. et al. (1991). "Structure and Activity of Composite Oxide Supported Platinum-Iridium Catalysts," Applied Catalysts 74: 65-81.
Tao, Y.-T. (May 1993). "Structural Comparison of Self-Assembled Monolayers of n-Alkanoic Acids on the surfaces of Silver, Copper, and Aluminum," J. Am. Chem. Soc. 115(10):4350-4358.
Ünal, N. et al. (Nov. 2011). "Influence of WC Particles on the Microstructural and Mechanical Properties of 3 mol% Y2O3 Stabilized ZrO2 Matrix Composites Produced by Hot Pressing," Journal of the European Ceramic Society (31)13: 2267-2275.
Zou, J. et al. (Jun. 4, 2004). "Solution Synthesis of Ultrastable Luminescent Siloxane-Coated Silicon Nanoparticles," Nano Letters 4(7):1181-1186.
U.S. Appl. No. 13/291,983, filed Nov. 8, 2011, for Layman et al.
U.S. Appl. No. 12/152,084, filed May 9, 2008, for Biberger.
U.S. Appl. No. 13/028,693, filed Feb. 16, 2011, for Biberger.
U.S. Appl. No. 12/152,111, filed May 9, 2008, for Biberger et al.
U.S. Appl. No. 12/151,830, filed May 8, 2008, for Biberger et al.
U.S. Appl. No. 12/968,248, filed Dec. 14, 2010, for Biberger.
U.S. Appl. No. 12/968,245, filed Dec. 14, 2010, for Biberger.
U.S. Appl. No. 12/968,241, filed Dec. 14, 2010, for Biberger.
U.S. Appl. No. 12/968,239, filed Dec. 14, 2010, for Biberger.
U.S. Appl. No. 12/969,128, filed Dec. 15, 2010, for Biberger.
U.S. Appl. No. 12/962,463, filed Dec. 7, 2010, for Leamon.
U.S. Appl. No. 12/961,030, filed Dec. 6, 2010, for Lehman.
U.S. Appl. No. 12/961,108, filed Dec. 6, 2010, for Lehman.
U.S. Appl. No. 12/961,200, filed Dec. 6, 2010, for Lehman.
U.S. Appl. No. 12/968,253, filed Dec. 14, 2010, for Biberger.
U.S. Appl. No. 12/968,235, filed Dec. 14, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/969,087, filed Dec. 15, 2010, for Biberger.
U.S. Appl. No. 12/962,533, filed Dec. 7, 2010, for Yin et al.
U.S. Appl. No. 12/962,523, filed Dec. 7, 2010, for Yin et al.
U.S. Appl. No. 12/001,643, filed Dec. 11, 2007, for Biberger et al.
U.S. Appl. No. 12/474,081, filed May 28, 2009, for Biberger et al.
U.S. Appl. No. 12/001,602, filed Dec. 11, 2007, for Biberger et al.
U.S. Appl. No. 12/001,644, filed Dec. 11, 2007, for Biberger et al.
U.S. Appl. No. 12/969,457, filed Nov. 15, 2010, for Leamon et al.
U.S. Appl. No. 12/969,503, filed Nov. 15, 2010, for Leamon et al.
U.S. Appl. No. 12/954,813, filed Nov. 26, 2010, for Biberger.
U.S. Appl. No. 12/954,822, filed Nov. 26, 2010, for Biberger.
U.S. Appl. No. 13/033,514, filed Feb. 23, 2011, for Biberger et al.
U.S. Appl. No. 13/589,024, filed Aug. 17, 2012, for Yin et al.
U.S. Appl. No. 13/801,726, filed Mar. 13, 2013, for Qi et al.

* cited by examiner

MICROWAVE PURIFICATION PROCESS

CROSS-REFERENCE TO RELATED APPLICATIONS

The present application is a divisional application of co-pending U.S. patent application Ser. No. 12/152,095, filed on May 9, 2008, and entitled "MICROWAVE PURIFICATION PROCESS," which claims priority to U.S. Provisional Application Ser. No. 60/928,946, filed May 11, 2007, entitled "MATERIAL PRODUCTION SYSTEM AND METHOD," both of which are hereby incorporated by reference as if set forth herein.

FIELD OF THE INVENTION

The present invention relates to the field of materials purification. More specifically, the present invention relates to a microwave-based purification process and system.

BACKGROUND OF THE INVENTION

In the powdered materials industry, there has become an increased interest in purer and purer powders. There are a variety of reasons for this interest. In the semiconductor industry, and more specifically the hard disk industry, there is a need for purer and purer metals. Components such as ¾" inch hard drives in cell phones and MP3 players can have up to six layers of metal on the mini-hard drives in order to achieve the storage capacity needed for video and other data. One of the metals that is used for coating is ruthenium. Here, the oxygen content is critical. If the oxygen content is too high, it can result in the formation of ruthenium-oxides, which are non-conductive. Non-conductivity poses problems when trying to store data.

FIG. 1 illustrates one example of powder particles 100 that are typically used in the materials industry. These powder particles 100 typically contain impurities, such as oxygen content 102 disposed around their core. The industry is looking for purification levels equal to or less than 200 ppm of oxygen in the starting powders. Currently, one attempted solution is to place the powder in a vacuum furnace or in a hydrogen-fired vacuum furnace on a tray. The furnace is brought up to relatively high temperatures. The oxygen content (and moisture) is desorbed from the powder. Hydrogen can flow over the powder to grab and remove the oxygen and moisture content, which is pumped out, leaving a purer powder.

The downside of these furnace technologies is that they require the use of high temperatures for a long period of time. One problem with this requirement is that it places a limitation on the minimum size of grain that can be purified. The smaller the grain size, the lower the sintering temperature is for the powder, thus making small grain powders difficult to purify using these technologies. What is needed is a more cost effective technology that allows relatively small grains to be purified without sintering.

These issues are important to the powder industry in general. Cutting tools can be formed from powders, such as tungsten-carbide, tungsten-nitride and the like. However, the powders often contain oxygen, sometimes in the form of thin oxygen layers formed around each particle. In sintering the powders together to form the cutting tools, it is desirable to maintain the powder-like nature. However, it is important to minimize the void between the particles. If the void is too big, the structural integrity of the end product suffers. If there is too much oxygen, the particles will not sufficiently sinter together. When using a cutting tool made from powders having these deficiencies, the lack of structural integrity can cause the tool to fracture. What is needed is a better way to take oxygen out of powders, reduce the voids, and prepare the powders for sintering.

FIG. 2 illustrates one system 200 that has be used to try and purify powders. Here, the target powder 240 (for example, boron) is disposed in a crucible 230 that is housed within a microwave production chamber 210, such as a microwave oven. Hydrogen gas flows from a gas supply system 220 into the microwave production chamber 210 via a conduit or tube 225. As the hydrogen gas flows into the microwave production chamber 210 and the crucible 230, the microwave production chamber 210 generates and applies microwaves to the hydrogen gas, thereby forming a plasma 250 and creating hydrogen radicals, which flow over the target powder 240 and are drawn out of the chamber 210 along with oxygen content from the target powder. This drawing force is supplied by a vacuum pump 260. Although this system removes a portion of the oxygen content, there is a problem with having the target powder being exposed to the energy of the microwaves. In this configuration, the target powder can loosely couple to the microwave and heat up. This parasitic heating can result in the powder being crystallized. In circumstances where amorphous powders are preferred, this crystallization is highly undesirable.

Therefore, what is needed in the art is an efficient and cost effective system and method of removing oxygen content from a target powder, while avoiding or minimizing any parasitic heating.

SUMMARY OF THE INVENTION

In one aspect of the present invention, a method of purifying a target powder having an oxygen content is provided. The method comprises flowing hydrogen gas through a microwave production chamber and applying microwaves to the hydrogen gas as the hydrogen gas flows through the microwave production chamber, thereby forming hydrogen radicals from the hydrogen gas. The hydrogen radicals flow out of the microwave production chamber to a target powder disposed outside of the microwave production chamber, where they are applied to the target powder, thereby removing a portion of the oxygen content from the target powder.

In another aspect of the present invention, a microwave purification system is provided. The system comprises a gas supply system configured to provide hydrogen gas and a microwave production chamber fluidly coupled to the gas supply system. The microwave production chamber is configured to receive hydrogen gas from the gas supply system and apply microwaves to the hydrogen gas, thereby forming hydrogen radicals. A target chamber is disposed outside of and fluidly coupled to the microwave production chamber. The target chamber is configured to receive the hydrogen radicals from the microwave production chamber and apply the hydrogen radicals to a target powder disposed within the target chamber, thereby removing a portion of oxygen content from the target powder.

In preferred embodiments, the target powder is housed within a target chamber. The hydrogen radicals flow into the target chamber and remove oxygen content from the target powder. The removed oxygen content then flows out of the target chamber.

In preferred embodiments, applying the hydrogen radicals to the target powder comprises the steps of agitating the target powder within the target chamber and flowing the hydrogen radicals through the target chamber as the target powder is being agitated.

Preferably, the target chamber houses a rotatable paddle wheel having an interior circumference and a plurality of paddles disposed in an annular configuration along the interior circumference. The target powder is disposed in the paddle wheel and the wheel is rotated as the hydrogen radical flow through the target chamber. In a preferred embodiment, the rotatable paddle wheel comprises a first end through which the hydrogen radicals enter and a second end through which the removed oxygen content exits. The rotatable paddle wheel extends from the first end to an expanding frusto-conical surface to a substantially cylindrical surface to a narrowing frusto-conical surface to the second end. The plurality of paddles are disposed on the substantially cylindrical surface.

In certain embodiments, the target chamber is heated prior to or during the step of applying the hydrogen radicals to the target powder. Preferably, the target chamber is heated to a temperature equal to or less than 1200 degrees Fahrenheit. Furthermore, the target powder can be heated prior to the step of applying the hydrogen radicals to the target powder.

In preferred embodiments, the step of flowing the hydrogen gas comprises applying a vacuum force to the hydrogen gas and the step of flowing the hydrogen radicals comprises applying a vacuum force to the hydrogen radicals.

Additionally, the step of applying microwaves to the hydrogen gas can result in the formation of hydrogen ions within the microwave production chamber. In certain embodiments, the method further comprises the steps of flowing the hydrogen ions out of the microwave production chamber to the target powder disposed outside of the microwave production chamber and applying the hydrogen ions to the target powder.

It is contemplated that a wide variety of target powder can be used in the present invention. Such target powders include, but are not limited to, boron and ruthenium.

DETAILED DESCRIPTION OF THE INVENTION

Figure 1:
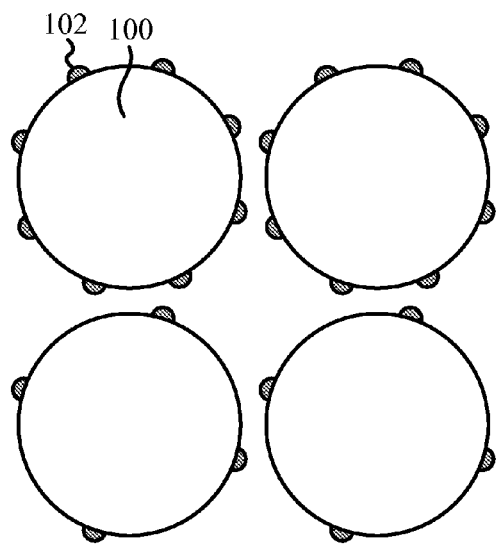
FIG. 1 illustrates a target powder having an oxygen content.
Figure 2:
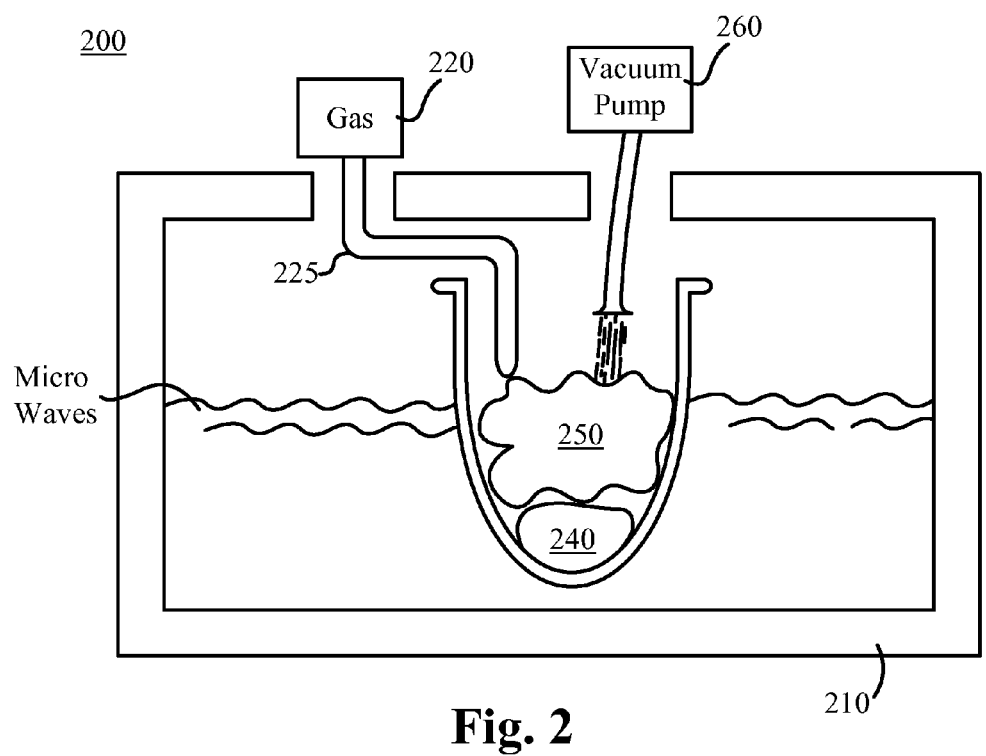
FIG. 2 illustrates a prior art powder purification system.

The description below concerns several embodiments of the invention. The discussion references the illustrated preferred embodiment. However, various modifications to the described embodiments will be readily apparent to those skilled in the art, and the generic principles herein may be applied to other embodiments. Therefore, the scope of the present invention is not limited to either the illustrated embodiment, nor is it limited to those discussed. To the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles. Powders that fall within the scope of the present invention may include, but are not limited to, any of the following: (a) nano-structured powders (nano-powders), having an average grain size less than 250 nanometers and an aspect ratio between one and one million; (b) submicron powders, having an average grain size less than 1 micron and an aspect ratio between one and one million; (c) ultra-fine powders, having an average grain size less than 100 microns and an aspect ratio between one and one million; and (d) fine powders, having an average grain size less than 500 microns and an aspect ratio between one and one million.

The present invention will be readily understood by the following detailed description in conjunction with the accompanying drawings. To facilitate this description, like reference numerals designate like elements.

Figure 3:
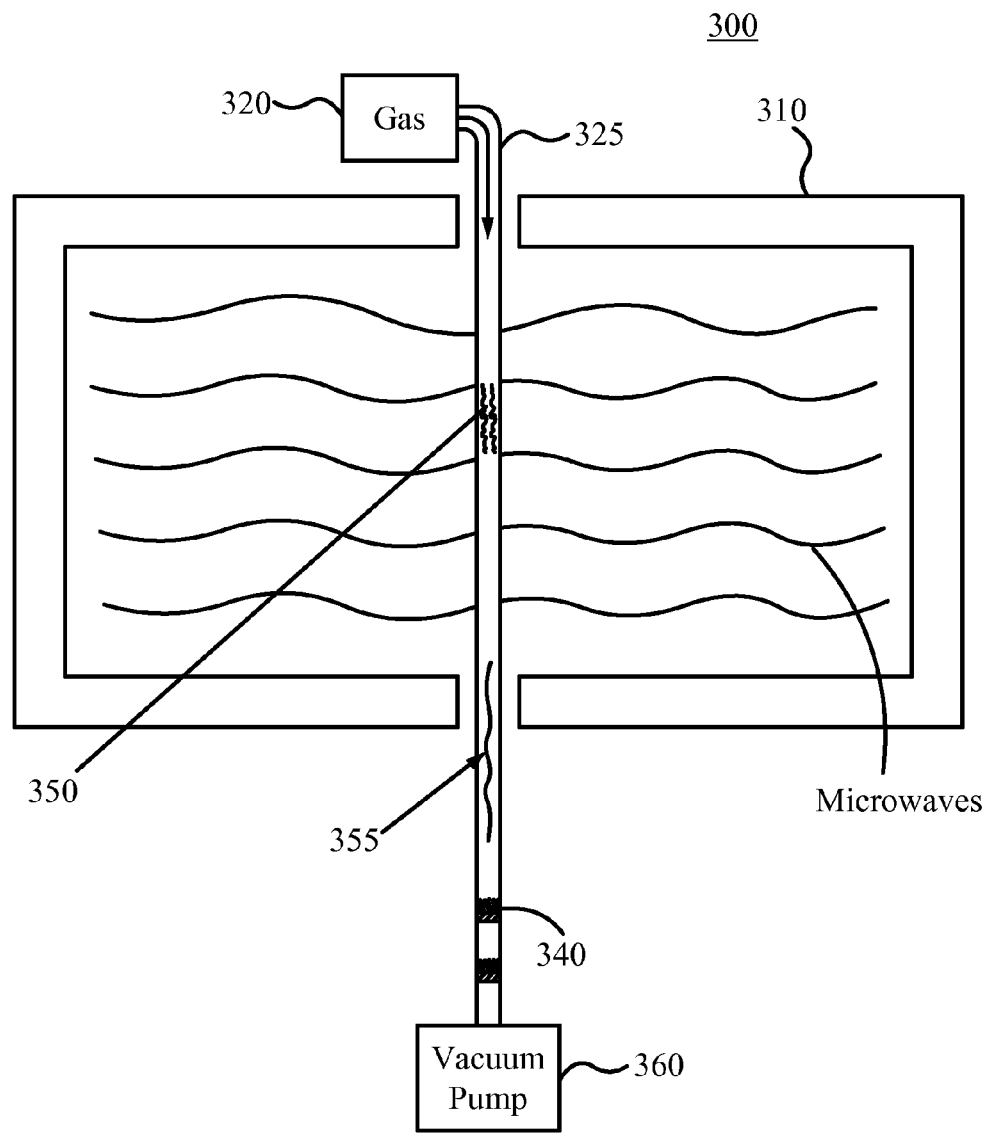
FIG. 3 illustrates one embodiment of a microwave purification system in accordance with the principles of the present invention.

FIG. 3 illustrates one embodiment of a microwave purification system 300 in accordance with the principles of the present invention. The system 300 comprises a microwave production chamber 310 configured to generate microwaves, a gas supply system 320 configured to provide a gas (preferably hydrogen), and a vacuum pump 360 fluidly coupled to the gas supply system 320 via a conduit or tube 325 that runs into and out of the microwave production chamber 310.

In operation, the vacuum pump 360 draws the hydrogen gas from the gas supply system 320 through the conduit 325 and into the microwave production chamber 310. Here, the microwave production chamber 310 produces microwaves, which are applied to the hydrogen gas to strike a plasma 350. As a result, hydrogen radicals 355 are formed. The hydrogen radicals 355 are then drawn out of the microwave production chamber 310 by the vacuum pump 360 and are applied to the target powder 340, which is disposed out of the microwave production chamber 310. The target powder 340 can be contained within a crucible in fluid communication with the conduit 325. The hydrogen radicals 355 react with the oxygen content of the powder 340, thereby disassociating the oxygen content from the powder. The removed oxygen content can then be drawn further away from the powder by the vacuum pump.

In addition to the hydrogen radicals 355, it is contemplated that hydrogen ions (i.e., hydrogen plasma) can also be formed in the microwave production chamber 310. At a low enough pressure, the glow discharge of the hydrogen plasma 355 can be drawn out to the target powder 340 by the vacuum pump 360. The hydrogen plasma can be applied to the target powder 340 to aid in the removal of the oxygen content.

By disposing the target powder 340 outside of the microwave production chamber 310 (i.e., out of the pathway of the microwaves), the system 300 can subject the target powder 340 to hydrogen radicals and ions, while avoiding the microwave energy and the parasitic heating associated with it.

Additionally, it is contemplated that the target powder 340 can be heating at a controlled rate prior to or during its exposure to the hydrogen radicals. This heating can aid in the chemical reactivity of the hydrogen and ablate or drive off moisture on the target powder 340.

Figure 4:
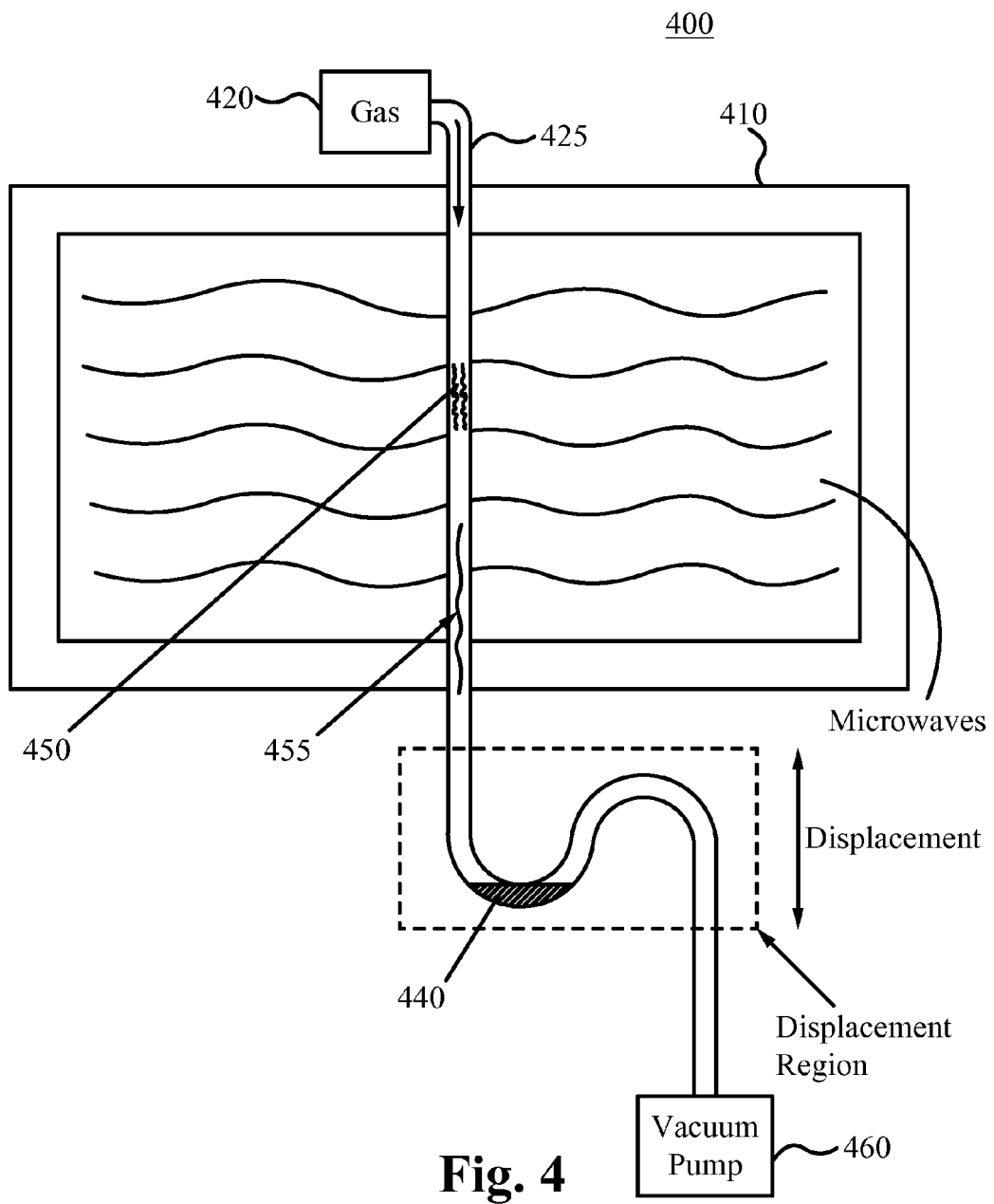
FIG. 4 illustrates another embodiment of a microwave purification system in accordance with the principles of the present invention.

FIG. 4 illustrates another embodiment of a microwave purification system 400 in accordance with the principles of the present invention. The system 400 comprises a microwave production chamber 410 configured to generate microwaves, a gas supply system 420 configured to provide a gas (preferably hydrogen), and a vacuum pump 460 fluidly coupled to the gas supply system 420 via a conduit or tube 425 that runs into and out of the microwave production chamber 410. Upon exiting the microwave production chamber 410, the conduit 425 can gooseneck or bend within a displacement region. In a preferred embodiment, the conduit 425 is configured to be agitated in the direction of the displacement arrows in order to shake up the target powder 440.

In operation, the vacuum pump 460 draws the hydrogen gas from the gas supply system 420 through the conduit 425 and into the microwave production chamber 410. Here, the microwave production chamber 410 produces microwaves, which are applied to the hydrogen gas to strike a plasma 450. As a result, hydrogen radicals 455 are formed. The hydrogen radicals 455 are then drawn out of the microwave production chamber 410 by the vacuum pump 460 and are applied to the target powder 440, which is disposed out of the microwave production chamber 410. The target powder 440 can be contained within a crucible in fluid communication with the conduit 425. The hydrogen radicals react with the oxygen content of the powder 440, thereby disassociating the oxygen content from the powder. The removed oxygen content can then be drawn further away from the powder by the vacuum pump.

In addition to the hydrogen radicals, it is contemplated that hydrogen ions (i.e., hydrogen plasma) can also be formed in the microwave production chamber 410. At a low enough pressure, the glow discharge of the hydrogen plasma 450 can be drawn out to the target powder 440 by the vacuum pump 460. The hydrogen plasma can be applied to the target powder 440 to aid in the removal of the oxygen content.

By disposing the target powder 440 outside of the microwave production chamber 410 (i.e., out of the pathway of the microwaves), the system 400 can subject the target powder 440 to hydrogen radicals and ions, while avoiding the microwave energy and the parasitic heating associated with it.

Additionally, it is contemplated that the target powder 440 can be heating at a controlled rate prior to or during its exposure to the hydrogen radicals. This heating can aid in the chemical reactivity of the hydrogen and ablate or drive off moisture on the target powder 440.

Although not shown in FIGS. 3 and 4, it is contemplated that the conduits can run through the microwave production chambers through airtight seals.

Figure 5:
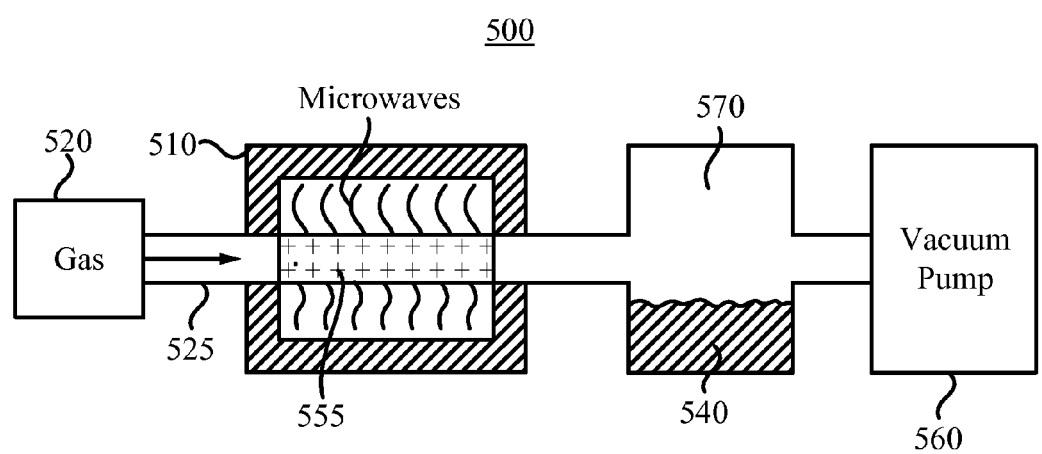
FIG. 5 illustrates yet another embodiment of a microwave purification system in accordance with the principles of the present invention.

FIG. 5 illustrates yet another embodiment of a microwave purification system 500 in accordance with the principles of the present invention. The system 500 comprises a microwave production chamber 510 configured to generate microwaves, a gas supply system 520 configured to provide a gas (preferably hydrogen), a target chamber 570 fluidly coupled to the microwave production chamber 510, preferably via a conduit or tube 525 that runs into and out of the microwave production chamber 510. A vacuum pump 560 is fluidly coupled to the target chamber 570, the microwave production chamber 510, and the gas supply system 520.

The target powder 540 is housed within the target chamber 570. In a preferred embodiment, the target chamber 570 is configured to agitate the target powder 540. Such agitation can be achieved in a variety of ways.

In operation, the vacuum pump 560 draws the hydrogen gas from the gas supply system 520 through the conduit 525 and into the microwave production chamber 510. Here, the microwave production chamber 510 produces microwaves, which are applied to the hydrogen gas to strike a plasma. As a result, hydrogen radicals 555 are formed. The hydrogen radicals 555 are then drawn out of the microwave production chamber 510 by the vacuum pump 560 and into the target chamber 570, where they are applied to the target powder 540 disposed therein. Some of the hydrogen radicals 555 flow straight through the target chamber 570 without reacting with the oxygen content of the target powder 540. However, some of the hydrogen radicals 555 do react with the oxygen content of the target powder 540, thereby disassociating the oxygen content from the powder. The removed oxygen content can then be drawn out of the target chamber 570 by the vacuum pump.

In order to maximize exposure of the target powder 540 to the hydrogen radicals 555, the target chamber preferably agitates the target powder 540 as the hydrogen radicals 555 flow through the target chamber 570. In a preferred embodiment, the target chamber 570 agitates the target powder 540 in such a way as to cause the powder to pass through the flow path of the hydrogen radicals.

In addition to the hydrogen radicals, it is contemplated that hydrogen ions (i.e., hydrogen plasma) can also be formed in the microwave production chamber 510. At a low enough pressure, the glow discharge of the hydrogen plasma can be drawn out to the target powder 540 by the vacuum pump 460. In a preferred embodiment, the hydrogen plasma discussed in FIGS. 3-5 is drawn out at a pressure equal to or less than approximately $1/350$ of an atmosphere. The hydrogen plasma can be applied to the target powder 540 to aid in the removal of the oxygen content.

By disposing the target powder 540 outside of the microwave production chamber 510 (i.e., out of the pathway of the microwaves), the system 500 can subject the target powder 540 to hydrogen radicals and ions, while avoiding the microwave energy and the parasitic heating associated with it.

Additionally, it is contemplated that the target powder 540 can be heating at a controlled rate prior to or during its exposure to the hydrogen radicals. This heating can aid in the chemical reactivity of the hydrogen and ablate or drive off moisture on the target powder 540.

Figure 6:
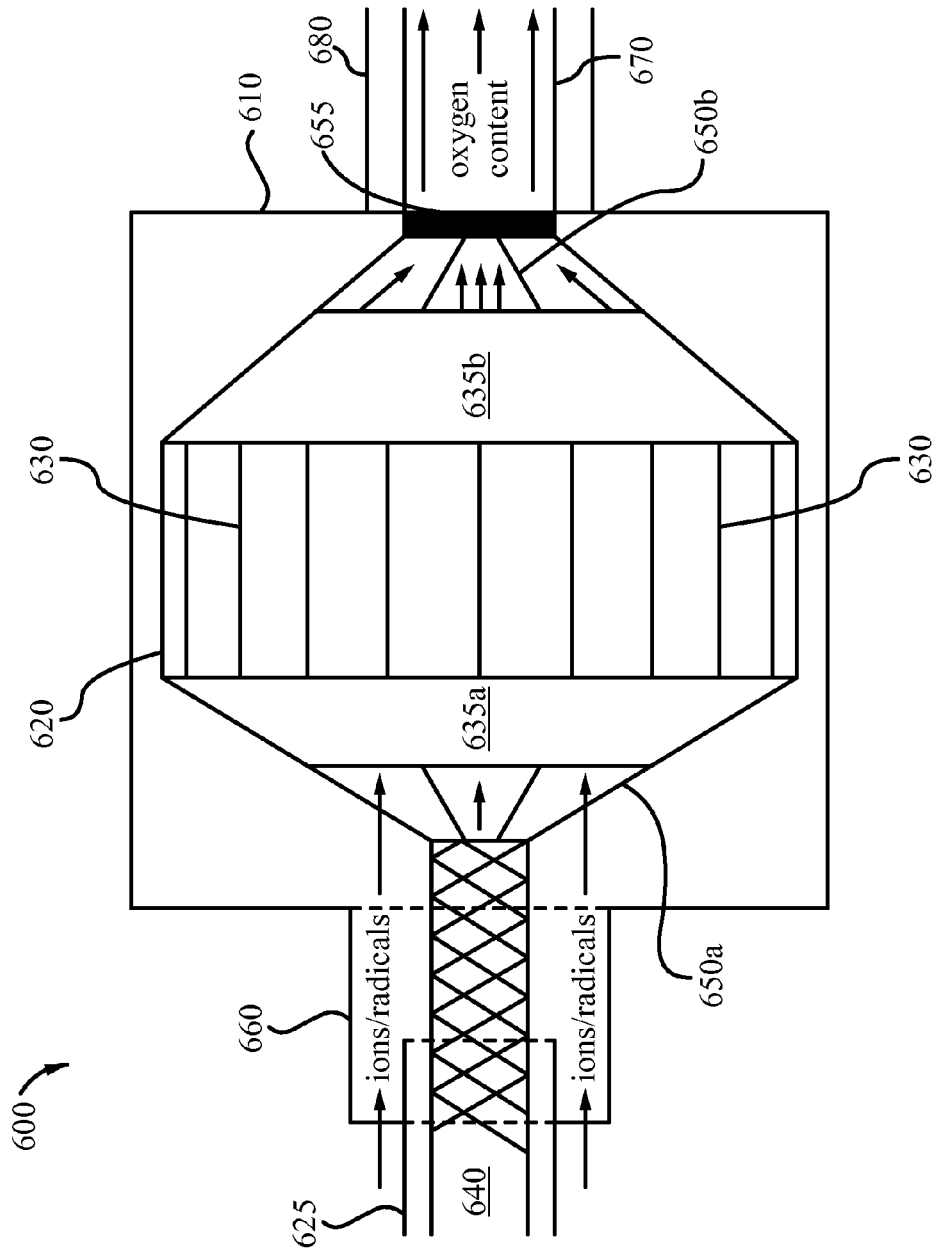
FIG. 6 illustrates a plan view of one embodiment of a target chamber in accordance with the principles of the present invention.

FIG. 6 illustrates one embodiment of a target chamber 600 in accordance with the principles of the present invention. In a preferred embodiment, the target chamber comprises a casing 610, preferably formed of metal so that it can be heated at a controlled rate as discussed above. The target chamber 600 is configured to agitate the target powder as the hydrogen radicals/ions flow through it via a gas supply conduit 660 fluidly coupled to the interior of the casing 610. Preferably, the gas supply conduit 660 is fluidly coupled to one of the microwave production chambers in FIGS. 3-5.

Within the casing 610 is housed a paddle wheel 620 configured to be rotated about a central axis. It is contemplated that the paddle wheel 620 can be rotated in a variety of ways, whether they be manual or automated. In a preferred embodiment, paddle wheel 620 is rotated by a shaft 640 to which it is coupled. Preferably, the interior of the casing 610 can be sealed off from any exterior contamination. The shaft 640 can be disposed within a rotary seal 625 that is connected to the gas supply conduit 660, thereby allowing the shaft 640 to rotate, while still preventing any contamination of the target powder within the casing 610 from external impurities.

In a preferred embodiment, the paddle wheel 620 comprises a first end through which the hydrogen radicals enter and a second end through which the removed oxygen content exits. The paddle wheel 620 preferably extends from the first end to an expanding frusto-conical surface 635a, to a substantially cylindrical surface, to a narrowing frusto-conical surface 635b, and finally to the second end. The frusto-conical surfaces aid in preventing the target powder from being drawn out of the paddle wheel 620 and the casing 610.

Figure 7:
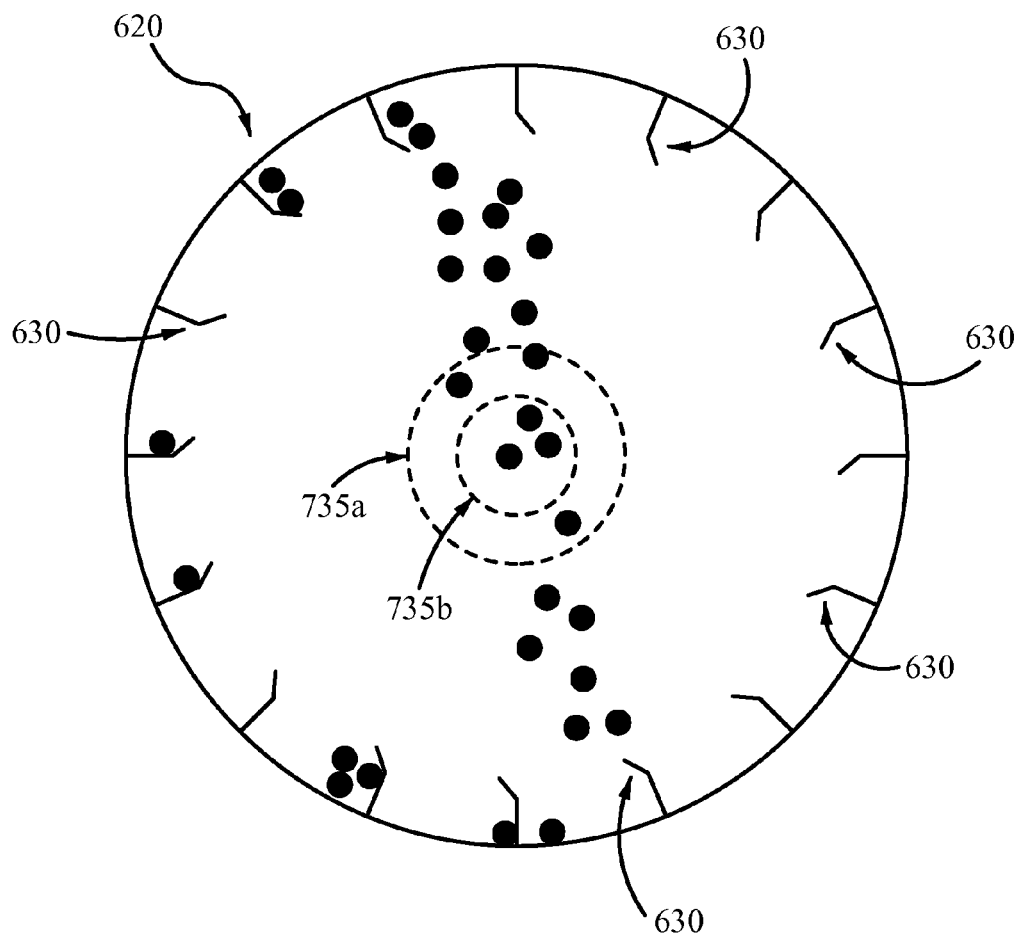
FIG. 7 illustrates one embodiment of a rotatable paddle wheel in accordance with the principles of the present invention.

The paddle wheel 620 has an interior circumference and a plurality of paddles 630 disposed in an annular configuration along the interior circumference. The paddles 630 can be uniformly-spaced or irregularly-spaced apart. During operation, the target powder is disposed in the paddle wheel 620. As the paddle wheel 620 rotates about its central axis, the paddles 630 lift a portion of the target powder up, then drop the target powder down through a location proximate the central axis in line with the flow if the radicals/ions, thereby maximizing the target powder's exposure to the radicals/ions. In a preferred embodiment, the plurality of paddles are disposed on the substantially cylindrical surface. As seen in FIG. 7, which is a view of the paddle wheel 620 from the perspective of looking through the gas supply conduit 660 in the direction of the radical/ion flow, the paddles 630 can be slightly angled or have a minor hook in order to aid in the lifting of the target powder.

Shaft 640 can be coupled to the first end of the paddle wheel 620 using spokes 650a. The second end of the paddle wheel 620 can be rotatably coupled to an oxygen content outlet 670 using spokes 650b and a rotary seal 655. An additional conduit 680 can be coupled to the casing 610 so as to cover oxygen content outlet 670. Oxygen content conduit 670 preferably extends into the casing 610 and is configured to receive the oxygen content flowing out of the paddle wheel 620 and the casing 610.

Referring back to FIG. 7, dotted line 735a represents the opening at the narrowest end of frusto-conical surface 635a (from FIG. 6) and dotted line 735b represents the opening at the narrowest end of frusto-conical surface 635b (from FIG. 6). In a preferred embodiment, the opening 735b is smaller in diameter than the opening 735a, as it can be helpful to minimize the exit opening 735b in order to prevent target powder from being drawn out of the paddle wheel and the casing. However, it is contemplated that a variety of size configurations can be employed.

Figure 8:
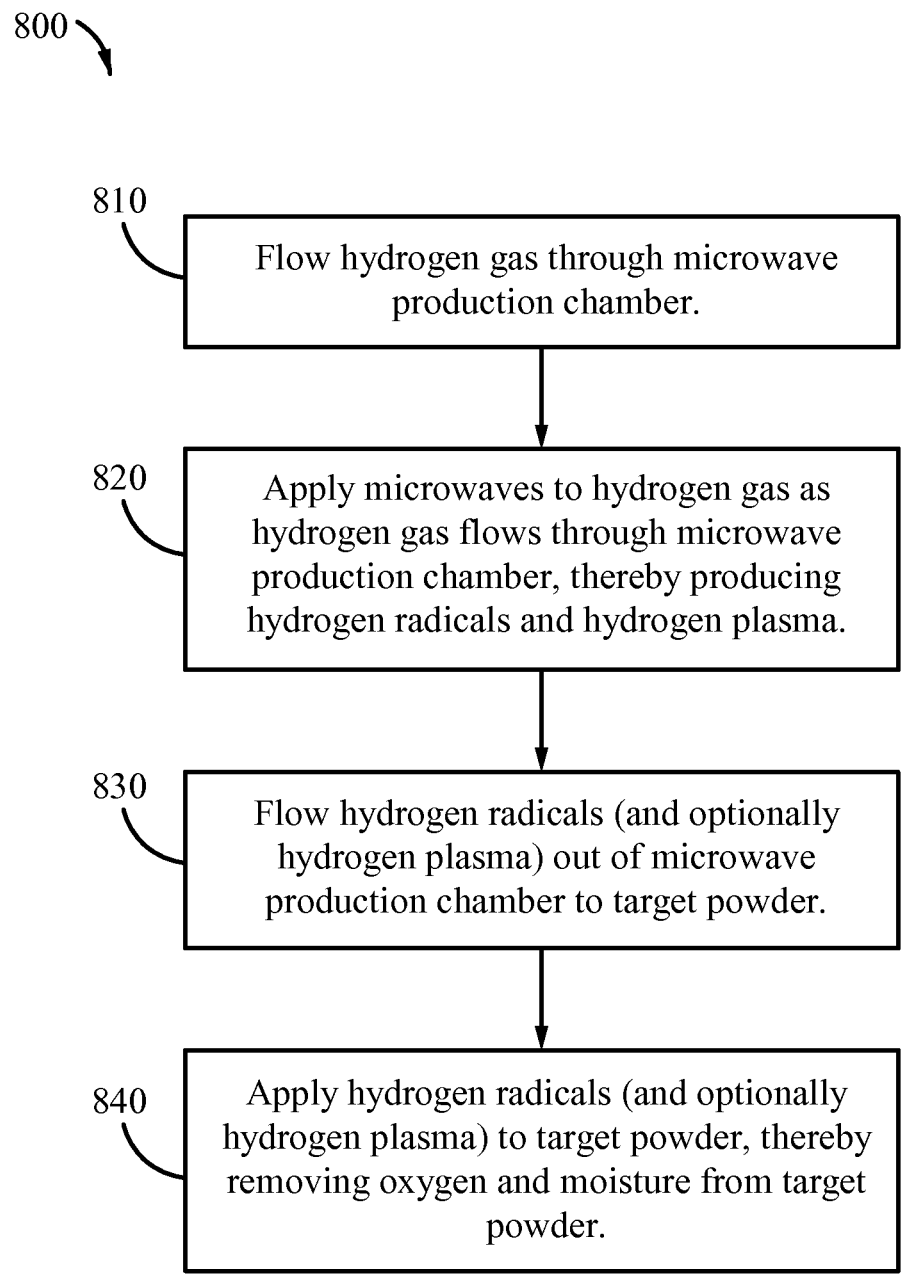
FIG. 8 is a flowchart illustrating one embodiment of a method of purifying powder in accordance with the principles of the present invention.

FIG. 8 is a flowchart illustrating one embodiment of a method 800 of purifying powder in accordance with the principles of the present invention. As would be appreciated by those of ordinary skill in the art, the protocols, processes, and procedures described herein may be repeated continuously or as often as necessary to satisfy the needs described herein. Additionally, although the steps of method 800 are shown in a specific order, certain steps may occur simultaneously or in a different order than is illustrated. Accordingly, the method steps of the present invention should not be limited to any particular order unless either explicitly or implicitly stated.

At step 810, hydrogen gas flows through a microwave production chamber. In a preferred embodiment, the hydrogen gas is supplied by a gas supply system and is drawn out by a vacuum pump through a conduit.

At step 820, the microwave production chamber generates and applies microwaves to the hydrogen gas as the hydrogen gas flows through the microwave production chamber, thereby forming hydrogen radicals from the hydrogen gas. Hydrogen ions/plasma can be formed as well.

At step 830, the hydrogen radicals, and possibly the hydrogen ions/plasma flow out of the microwave production chamber to a target powder disposed outside of the microwave production chamber. In a preferred embodiment, the target powder is housed within a target chamber, preferably configured to agitate the target powder as discussed above.

At step 840, the hydrogen radicals, and possibly the hydrogen ions/plasma, are applied to the target powder. The hydrogen ions react with oxygen content of the target powder, thereby removing a portion of the oxygen content from the target powder. This removed oxygen content can then be drawn away from the target powder, preferably out of the target chamber.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A microwave purification system comprising:
a gas supply system configured to provide hydrogen gas;
a microwave production chamber fluidly coupled to the gas supply system, wherein the microwave production chamber is configured to receive hydrogen gas from the gas supply system and apply microwaves to the hydrogen gas, thereby forming hydrogen radicals; and
a target chamber disposed outside of and fluidly coupled to the microwave production chamber, wherein the target chamber is configured to receive the hydrogen radicals from the microwave production chamber and apply the hydrogen radicals to a target powder disposed within the target chamber, thereby removing a portion of oxygen content from the target powder.

2. The system of claim 1, wherein the target chamber comprises an outlet and a vacuum pump is fluidly coupled to the outlet, the vacuum pump being configured to draw the hydrogen gas from the gas supply system to the microwave production chamber, draw the hydrogen radicals from the microwave production chamber to the target chamber, and draw the removed portion of oxygen content out of the target chamber.

3. The system of claim 2, wherein the target chamber is further configured to agitate the target powder as the hydrogen radicals are being applied to the target powder.

4. The system of claim 3, wherein the target chamber houses a paddle wheel having an interior circumference and a plurality of paddles disposed in an annular configuration along the interior circumference, the target powder disposed in the paddle wheel, the paddle wheel being configured to rotate about a central axis, lift a portion of the target powder up during rotation, and drop the target powder down through a location proximate the central axis.

5. The system of claim 4, wherein the rotatable paddle wheel comprises a first end through which the hydrogen radicals enter and a second end through which the removed oxygen content exits, the rotatable paddle wheel extending from the first end to an expanding frusto-conical surface to a substantially cylindrical surface to a narrowing frusto-conical surface to the second end, the plurality of paddles being disposed on the substantially cylindrical surface.

6. The system of claim 4, wherein the target chamber is configured to be heat the target powder prior to receiving the hydrogen radicals.

7. The system of claim 1, wherein the target chamber is configured to be heat the target powder prior to receiving the hydrogen radicals.

* * * * *